(12) United States Patent
Lux

(10) Patent No.: US 11,439,339 B1
(45) Date of Patent: Sep. 13, 2022

(54) METHOD AND SYSTEM FOR MEASURING CARDIAC TISSUE HEALTH BASED ON $DV/DT_{min}$ OF A DEPOLARIZATION WAVE WITHIN A CARDIAC ELECTROGRAM

(71) Applicant: Neucures Inc., Los Angeles, CA (US)

(72) Inventor: Robert L. Lux, Park City, UT (US)

(73) Assignee: NEUCURES INC., Los Angeles, CA (US)

( * ) Notice: Subject to any disclaimer, the term of this patent is extended or adjusted under 35 U.S.C. 154(b) by 0 days.

(21) Appl. No.: 17/073,230

(22) Filed: Oct. 16, 2020

(51) Int. Cl.
*A61B 5/349* (2021.01)

(52) U.S. Cl.
CPC .................... *A61B 5/349* (2021.01)

(58) Field of Classification Search
CPC ..................................................... A61B 5/349
See application file for complete search history.

(56) References Cited

U.S. PATENT DOCUMENTS

| | | | |
|---|---|---|---|
| 2016/0331258 A1* | 11/2016 | Du | A61B 5/316 |
| 2017/0156612 A1* | 6/2017 | Relan | A61B 5/363 |
| 2018/0289276 A1* | 10/2018 | Relan | A61B 5/6852 |

\* cited by examiner

*Primary Examiner* — Catherine M Voorhees
*Assistant Examiner* — Roland Dinga
(74) *Attorney, Agent, or Firm* — HM Law Group LLP; Vani Moodley, Esq.

(57) ABSTRACT

A method for determining cardiac tissue health based on a depolarization wave within an EGM is disclosed. The method includes computing a first derivative with respect to time (DV/DT) of the EGM, determining extrema for the first derivative, establishing a value $DV/DT_{MIN}$ based on the extrema and mapping the value $DV/DT_{MIN}$ to cardiac tissue.

12 Claims, 12 Drawing Sheets

Flow Chart for Determining Unipolar $DV/DT_{MIN}$

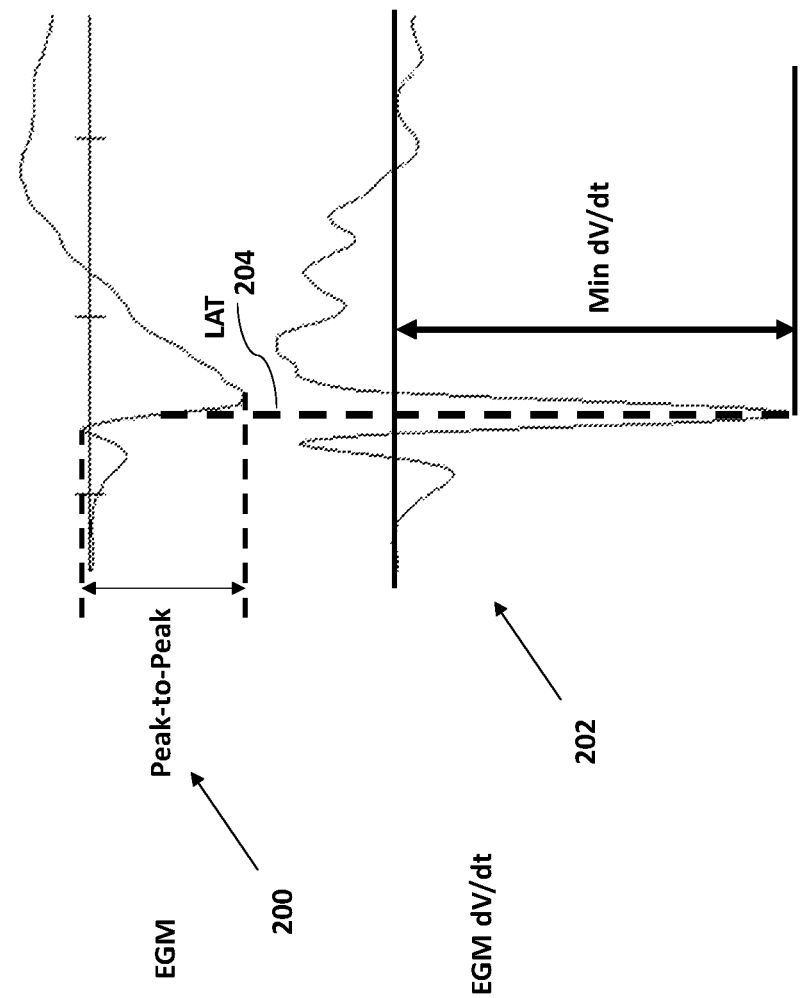
FIG. 2a. Determining LAT and Peak-to-Peak Voltage

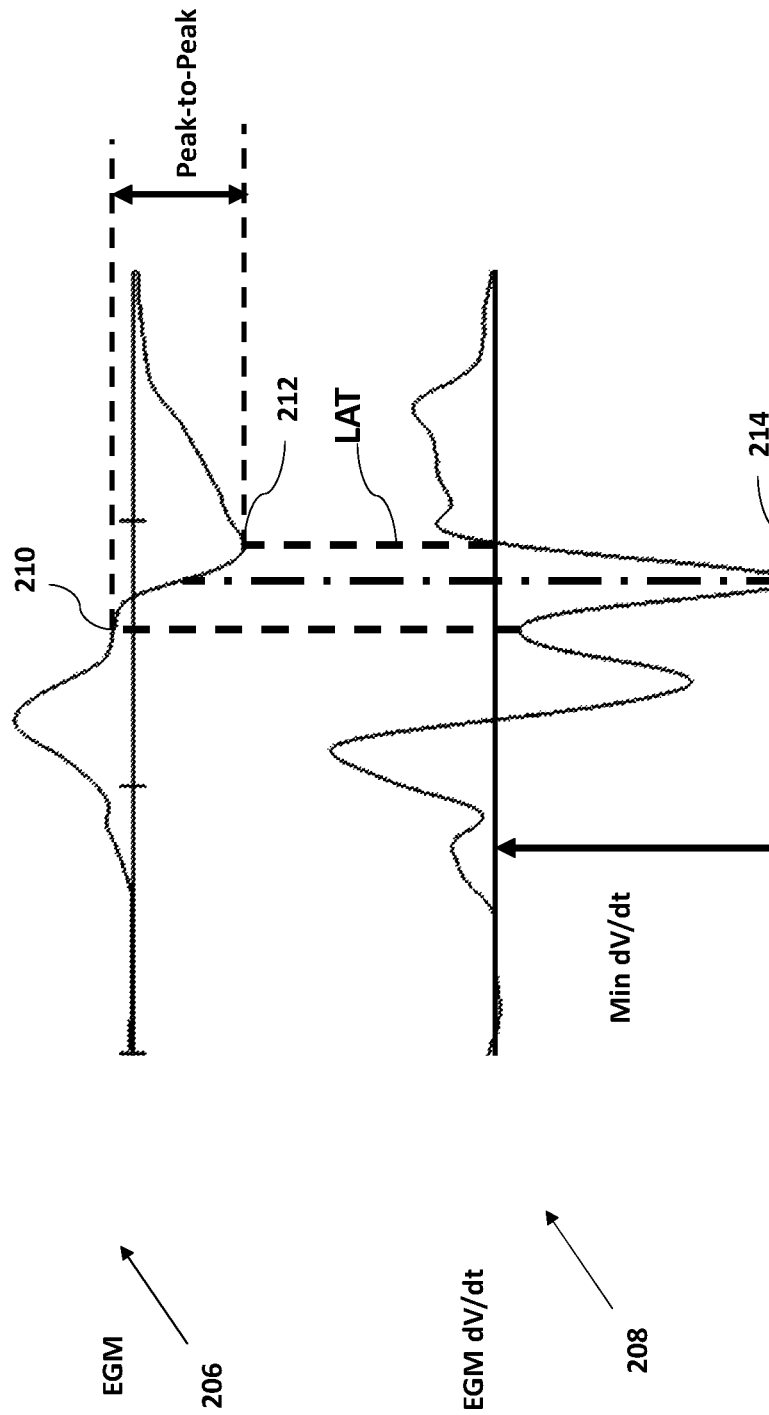

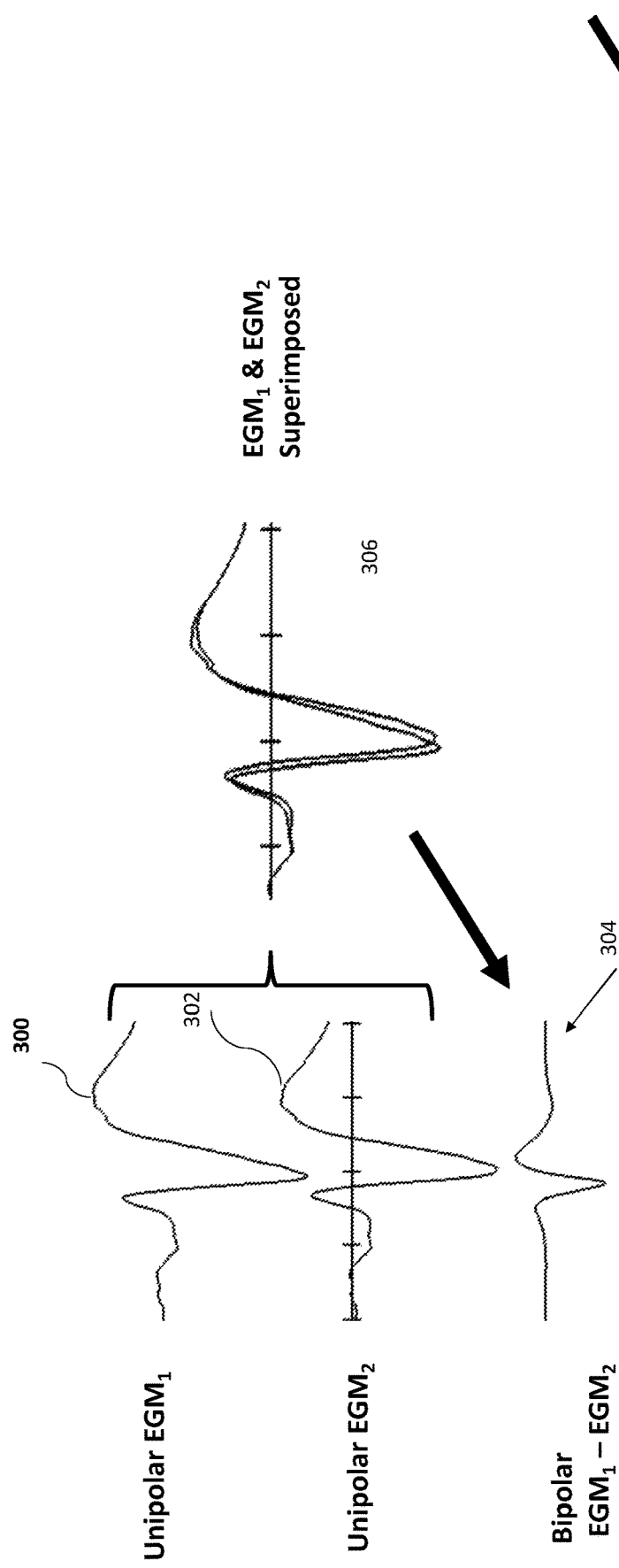
FIG 3. Constructing Bipolar EGM from two Unipolar EGMs

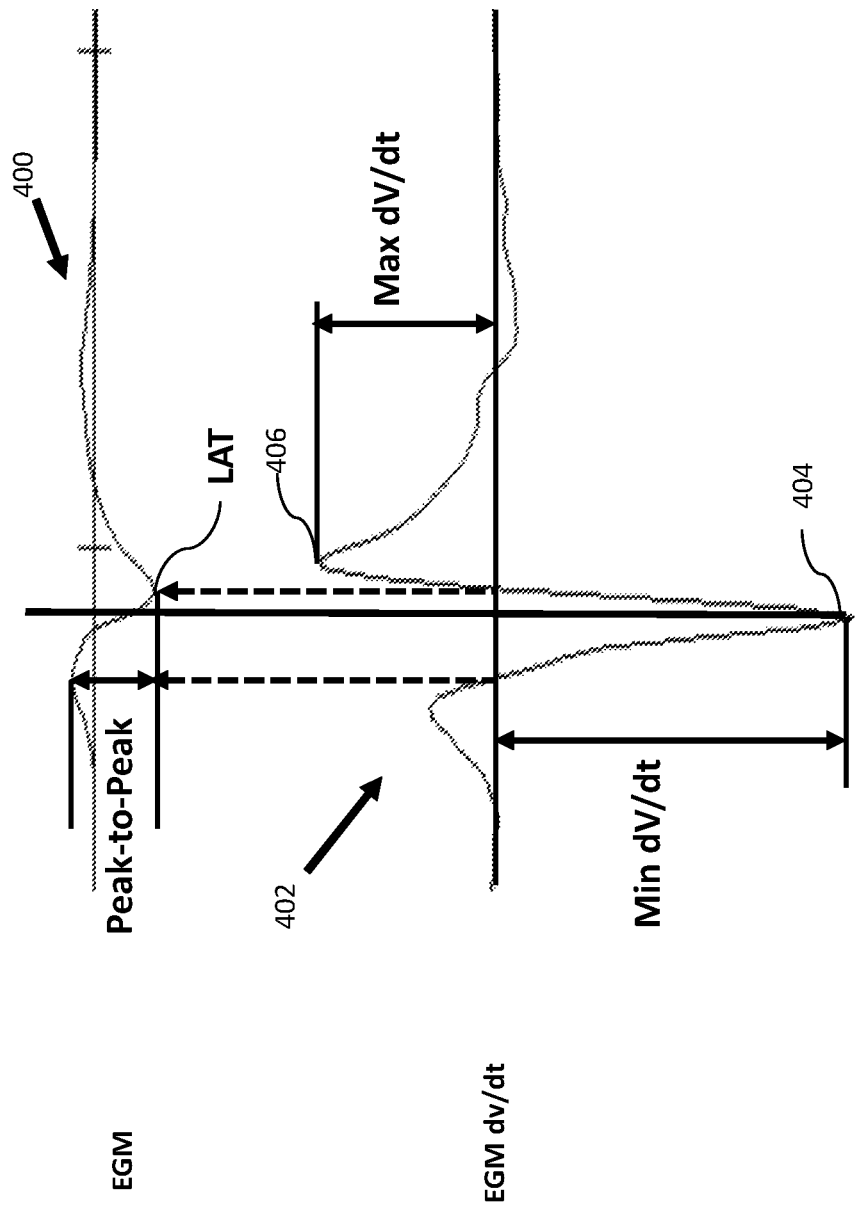

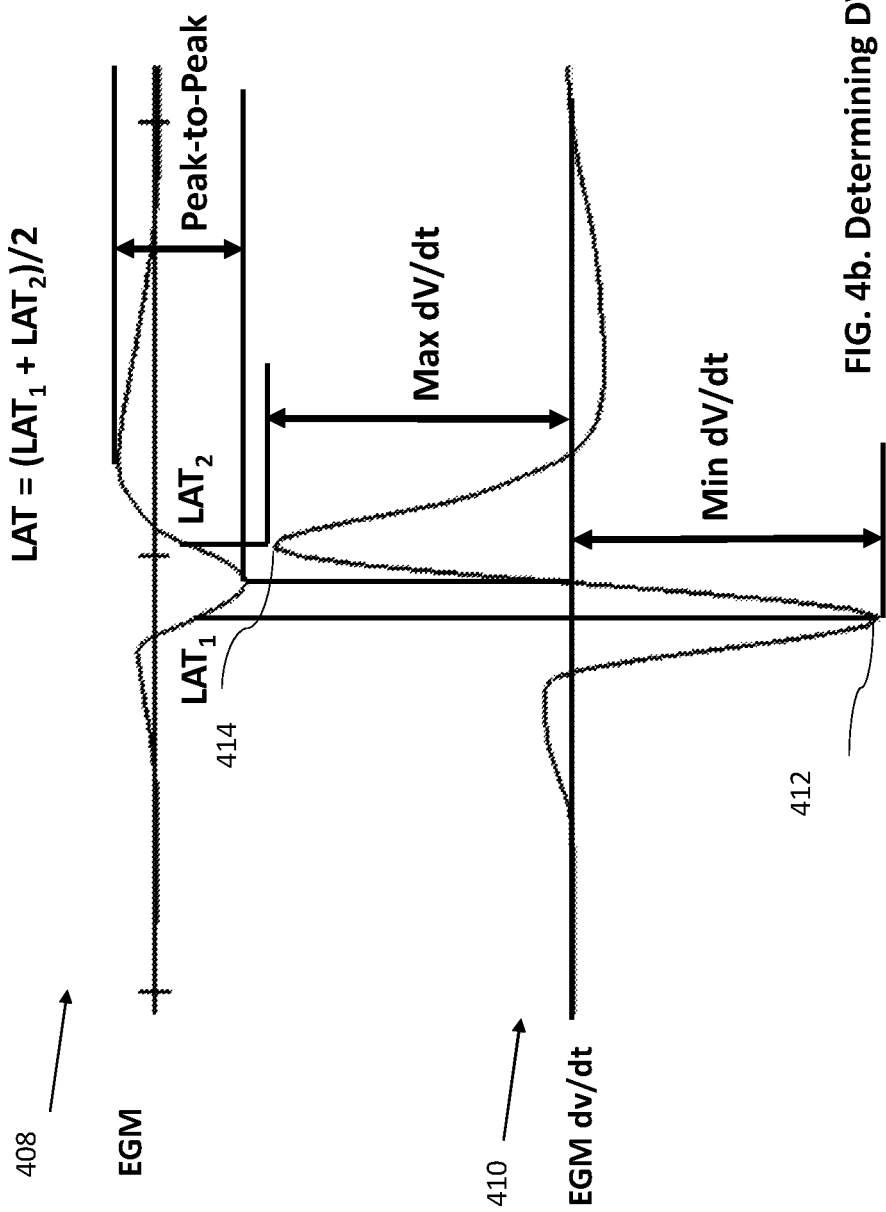

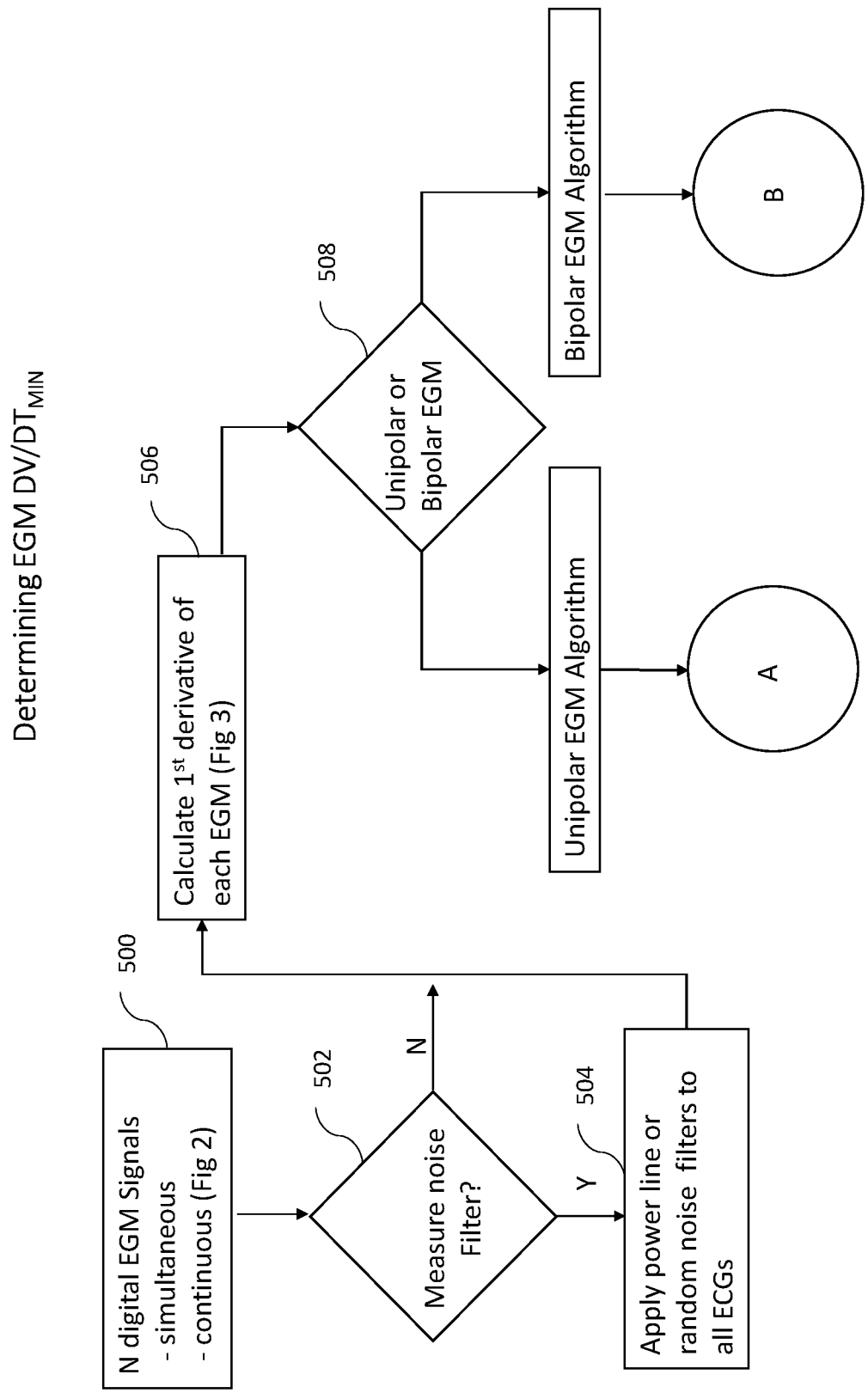
FIG 5a: A Flow Chart for Determining DV/DT$_{MIW}$

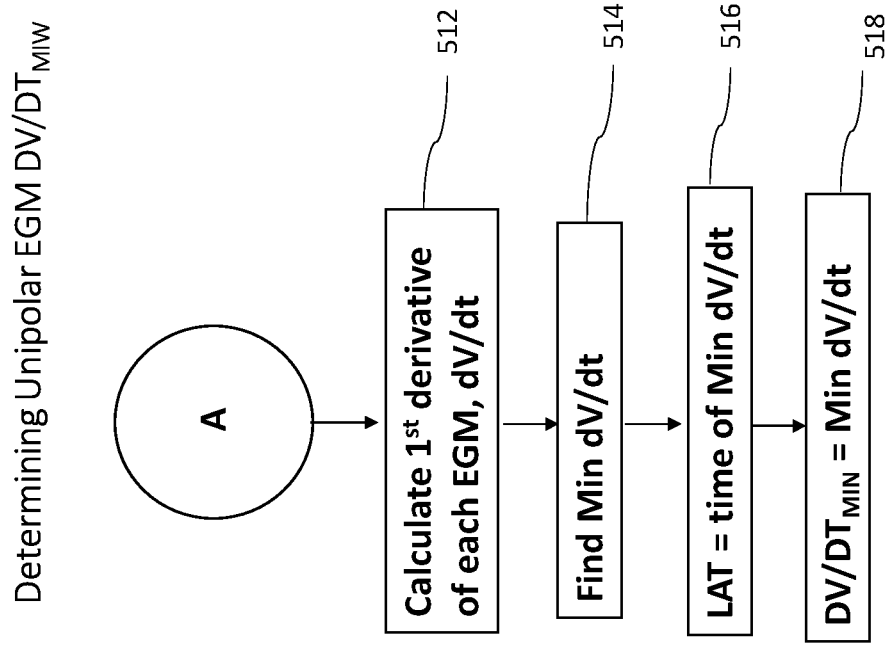
FIG 5b: Flow Chart for Determining Unipolar $DV/DT_{MIN}$

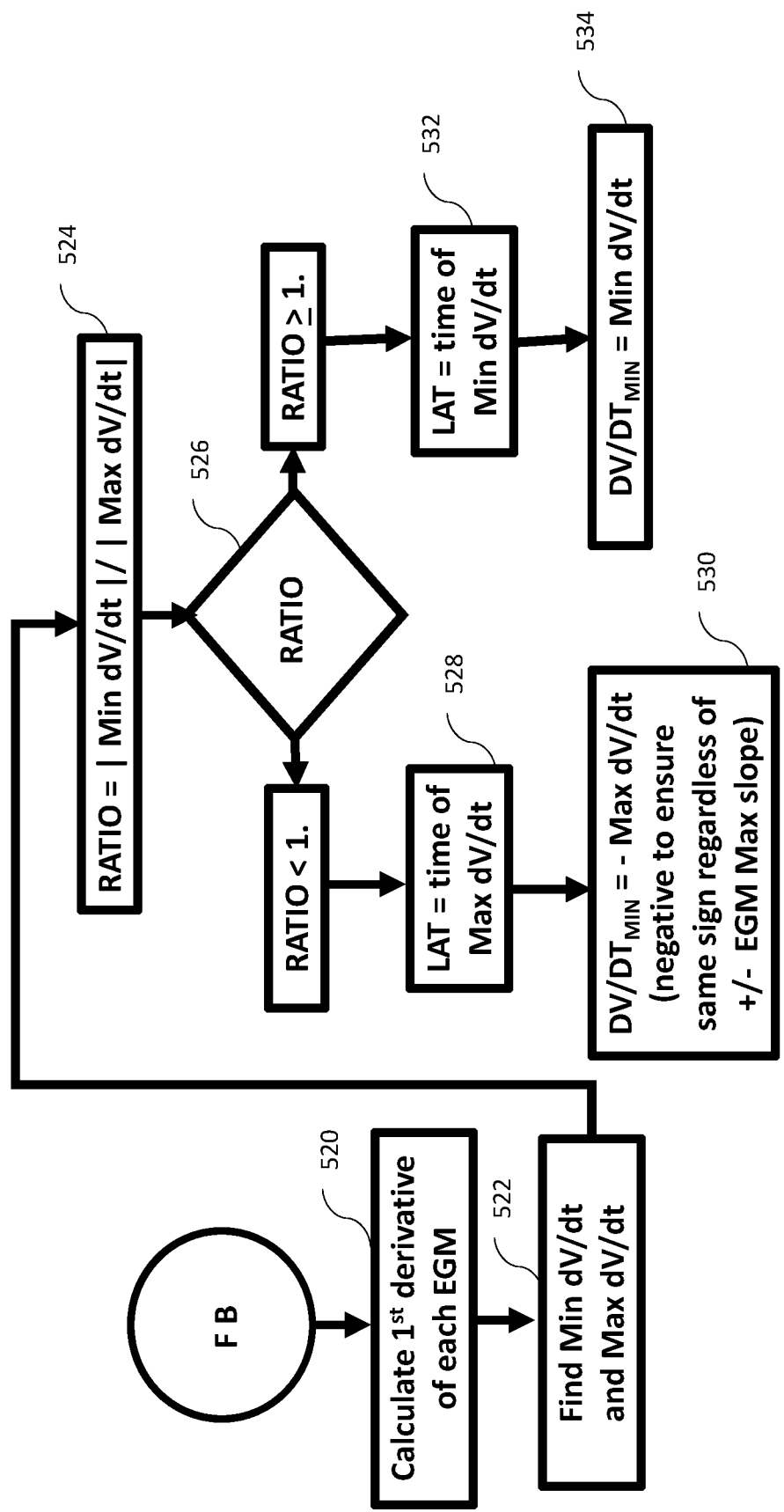
FIG. 5c: Flow Chart for Determining Bipolar LAT and DV/DT$_{MIN}$

ND SYSTEM FOR MEASURING
CARDIAC TISSUE HEALTH BASED ON
$DV/DT_{min}$ OF A DEPOLARIZATION WAVE
WITHIN A CARDIAC ELECTROGRAM

FIELD

Embodiments of the present invention relate to systems and methods for use in quantitating and characterizing a plurality of signals from the heart.

BACKGROUND

Electrical activity generated by the heart can be measured by arrays of electrodes placed on and within the cardiac muscle. The recorded tracings are called electrograms (EGMs). The dominant wave of EGMS, the depolarization wave, reflects the electrical depolarization (excitation) of the heart that leads to its contraction.

The depolarization wave of each EGM contains information about the health of the tissue near the electrode and quantitative measurements of the wave provide a means to separate normal and abnormal cardiac tissue

SUMMARY

Broadly, embodiments of the present invention disclose techniques for accurately determining depolarization voltage of each electrogram. The technique includes the following steps:

Determining the first derivative of the depolarization wave of each EGM, dV/dt

Determining the time of the minimum of the EGM derivative, the Local Activation Time (LAT) from the derivative during the depolarization wave;

Tabulating the value of the minimum value of the EGM derivative, $DV/DT_{MIN}$, as an index of cardiac tissue health close to the EGM electrode.

In one embodiment, a method for determining cardiac tissue health based on a depolarization wave within an EGM is provided. According to the method, a first derivative with respect to time (DV/DT) of the EGM is computed. Extrema for the first derivative is determined and a value of $DV/DT_{MIN}$ is established based on the extrema. The value of $DV/DT_{MIN}$ may be mapped to cardiac tissue.

In one embodiment, if the electrogram comprises a unipolar electrogram, then the value $DV/DT_{MIN}$ is established by selecting a minima from the extrema as the value for $DV/DT_{MIN}$.

In one embodiment, if the electrogram comprises a bipolar electrogram, then the value $DV/DT_{MIN}$ is established by selecting as one of a maxima and a minima from the extrema as the value for $DV/DT_{MIN}$ based on a ratio.

In one embodiment, the value for $DV/DT_{MIN}$ is selected as Min dV/dt when the ratio |Min dV/dt|/|Max dV/dt| is greater than or equal to one.

In one embodiment, the value for $DV/DT_{MIN}$ is selected as the minus Max dV/dt when the ratio |Min dV/dt|/|Max dV/dt| is less than one.

Other aspects of the invention, will be apparent from the written description below.

BRIEF DESCRIPTION OF THE DRAWINGS

FIGS. 2a & 2b show examples of unipolar EGMs and their first derivatives measured from cardiac muscle and measurements of LAT and $DV/DT_{MIN}$ are illustrated in accordance with one embodiment of the invention.

FIG. 3 shows an example of a construction of a bipolar EGM from two closely spaced unipolar EGMs, in accordance with one embodiment of the invention.

FIGS. 4a & 4b show examples of bipolar EGMs and their first derivatives with respect to time an illustrates aspects of aspects of how $DV/DT_{MIN}$ may be computed for the dominant and nondominant cases, in accordance with one embodiment of the invention.

FIGS. 5a-5c show flowcharts of techniques for computing $DV/DT_{MIN}$ from unipolar and bipolar EGMs, in accordance with one embodiment of the invention.

DETAILED DESCRIPTION

In the following description, for purposes of explanation, numerous specific details are set forth in order to provide a thorough understanding of the invention.

Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not others.

Moreover, although the following description contains many specifics for the purposes of illustration, anyone skilled in the art will appreciate that many variations and/or alterations to said details are within the scope of the present invention. Similarly, although many of the features of the present invention are described in terms of each other, or in conjunction with each other, one skilled in the art will appreciate that many of these features can be provided independently of other features. Accordingly, this description of the invention is set forth without any loss of generality to, and without imposing limitations upon, the invention.

As will be appreciated by one skilled in the art, the aspects of the present invention may be embodied as a system, method or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "circuit," "module," or "system." Furthermore, aspects of the present invention may take the form of a computer program product embodied in one or more computer readable medium(s) having computer readable program code embodied thereon.

Figure 1:
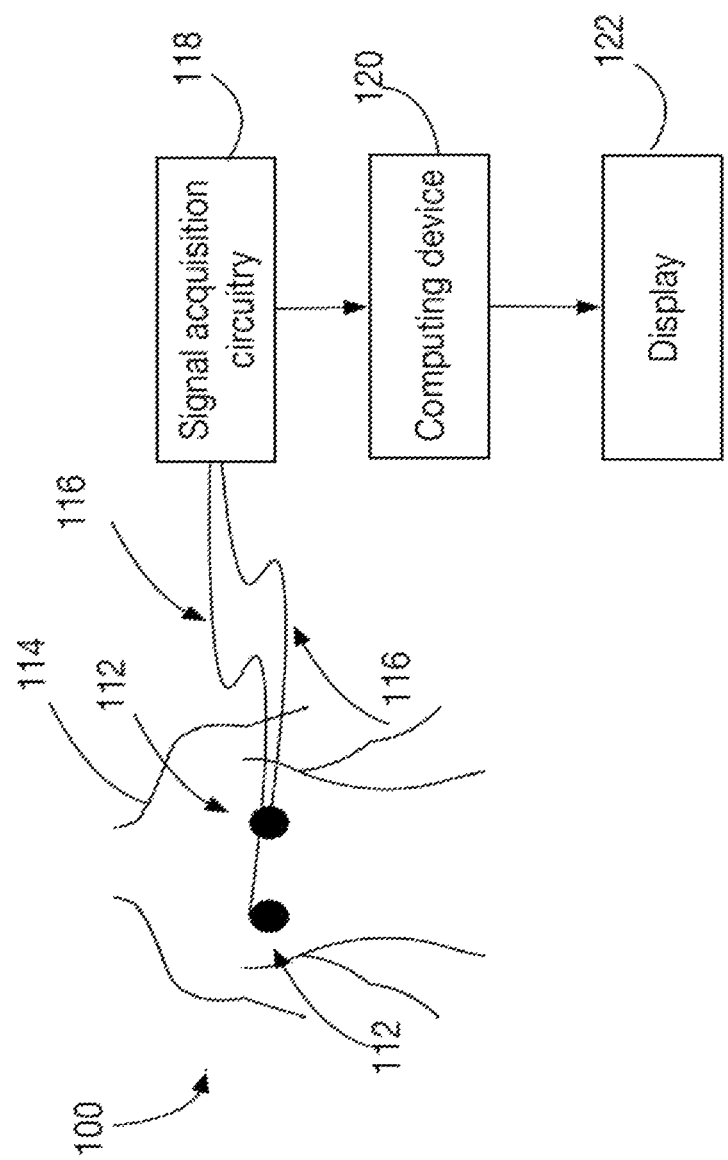
FIG. 1 shows an exemplary system for acquiring cardiac signals in accordance with one embodiment of the invention.

FIG. 1 of the drawings shows an exemplary system 100 for acquiring cardiac signals in accordance with one embodiment of the invention. As will be seen, the system 100 comprises a plurality of electrodes 112 that that may be positioned on the torso of a patient 114. The electrodes 112 may be configured to measure body-surface potentials of the patient 114, e.g. the torso-surface potentials (electrocardiograms or ECGs of a patient 114. Additional electrodes on catheters inserted into the heart cavity or on the heart surfaces collect signals called electrograms (EGMs). Each electrode (body surface or heart) I is coupled via an electrical lead 116 to interface/amplifier circuitry 118.

The interface/amplifier circuitry 118 may be configured to amplify the signals from the electrodes 112 and provide the signals to a computing device 120. In other embodiments, a wireless connection may be used to transmit the signals sensed by electrodes 112 to the interface/amplifier circuitry 118 and, in turn, the computing device 120, e.g., as channels of data. For example, the interface/amplifier circuitry 118 may be electrically coupled to each of the computing device 120 using, e.g., analog electrical connections, digital electrical connections, wireless connections, bus-based connections, network-based connections, internet-based connections, etc. The computing device 120 may be operatively coupled to a display device 122 for displaying information to an operator.

The device 120 may record and analyze the torso-surface potential signals sensed by electrodes 112 and amplified/conditioned by the interface/amplifier circuitry 118. The computing device 120 may be configured to analyze the signals from the electrodes 112 to provide electrical activation information or data such as cardiac electrical activation times, e.g., representative of actual, or local, electrical activation times of one or more regions of the patients heart as will be further described herein.

Additionally, the computing device 120 may be configured to provide graphical user interfaces depicting the electrical activation times obtained using the electrodes 112 on the display device 122.

EGMs represent the voltage signals which show a rapid change at the time of a heartbeat that corresponds to the propagating electrical wave that initiates contraction of the heart. Embodiments of the present invention disclosed techniques to measure the Local Activation Time (LAT) and $DV/DT_{MIN}$ of the depolarization wave in each EGM. The figures show graphically how the measurements are made.

Aspects of the depolarization wave relate specifically to the heart tissue local to the electrodes, including the minimum value of the first derivative of the EGM, $DV/DT_{MIN}$.

$DV/DT_{MIN}$ relates to the strength of the depolarization wave as it passes the electrode and reflects normality or abnormality of the cardiac tissue.

Referring now to FIG. 2a of the drawings, reference 200 generally indicates a unipolar EGM, whereas reference 202 indicates its first derivative DV/DT of the EGM with respect to time. In this case, LAT is said to be the time at which the first derivative DV/DT with respect to time is at a minimum. It is to be noted that the EGM 200 is characterized by a sharp down stroke at LAT time 204 in the DV/DT signal 202.

E fro 2b of the drawings shows another example of a unipolar EGM indicated generally by reference 206, whereas reference 208 indicates it first derivative DV/DT with respect to time. In this case, the EGM 206 has an inflection point 210 in its down stroke and reaches a minimum 212. As will be seen, the first derivative 208 of the EGM 206 comprises a minimum point 214 corresponding to that portion of the down slope in the EGM 204 between the inflection point 210 and the minimum point 212. The time of the minimum point 214 is taken to be the time for LAT.

FIG. 3 shows how a bipolar EGM can be constructed from two unipolar EGMs received from two closely spaced electrodes. Referring to FIG. 3, reference numerals 300 and 302 generally indicate two closely spaced unipolar EGMs, respectively. To calculate the bipolar EGM 304, the EGM 302 is subtracted from the EGM 300. Reference numeral 306 depicts a superimposition of EGMs 300 and 302. It is to be appreciated that the order of the subtraction (polarity of the EGM) is irrelevant.

FIG. 4a show an example of a bipolar EGM 400 and its first derivative DV/DT 402. As will be seen, the first derivative 402 comprises two extrema. The extrema include a minima 404 and a maxima 406. It will be seen that the minima 404 is much greater in magnitude than the maxima 406. For this case, the Local Activation Time (LAT) is set as the time of the derivative minimum magnitude, |Min dv/dt|, which as noted above is much greater than the derivative maximum, |Max dv/dt|. Thus, the bipolar EGM 402 represents a dominant case.

FIG. 4b shows an example of a bipolar EGM 408 and its first derivative DV/DT 41.0. The first derivative 410 includes a minima 412 and a maxima 414. As will be seen, the values for the minima 412 and maxima 414 are similar and thus no one value dominant over the other. Hence, the EGM 408 is referred to as the nondominant case. For this case, Local Activation Time (LAT) may be set as the average of the times at which the derivative is minimum in magnitude, |Min dv/dt| and the derivative is maximum (|Max dv/dt|). In this case, and in accordance with the embodiment of invention, $DV/DT_{MIN}$ may be as the Min dV/dt (negative by nature) or the negative of Max dV/dt, (minus Max dV/dt), as explained in the flowcharts in FIG. 5 and FIG. 6.

FIGS. 5a to 5c, show a flowchart of operations performed to calculate $DV/DT_{MIN}$ in accordance with one embodiment of the invention. Referring to FIG. 5a at block 500, N digital ECG signals may be simultaneously and continuously acquired from the unit 118. Processing block 502 may measure the noise level in the signals, and determine if the noise level is above a certain threshold in which case control passes to block 504 wherein noise reduction techniques are performed to remove or at least reduce the noise levels. Various techniques may be employed to remove noise detected in the signals. For example, power line or random noise filters may be applied to all ECGs.

Once the N ECG signals with appropriate noise levels are obtained, processing may be transitioned to block 506, wherein the first derivative with respect to time of each EGM is computed. At block 508, a determination is made to distinguish the EGMs as bipolar or unipolar. For unipolar EGMs, control process to block 512 (see FIG. 5a), and for bipolar EGMs, control passes to block 520 (see FIG. 5c).

Referring to FIG. 5b, at block 512 the first derivative with respect to time for each EGM is calculated. At block 514, the minima Min dV/dt in the first derivative is located. LAT is set to be the time at which the minima Min dV/dt occurs (block 516) and $DV/DT_{MIN}$ is set to Min dV/dt. The above steps for the unipolar case are illustrated in FIGS. 2a and 2b.

FIG. 5c shows the processing that occurs in the case of bipolar EGM's, in accordance with one embodiment of the invention. As will be seen, at block 520, the first derivative with respect to time is computed for each EGM. At block 522 values for Min dV/dt and Max dV/dt are determined. Control then passes to block 524 where the ratio |Min dV/dt|/|Max dV/dt| is determined. At block 526, the value of the ratio is evaluated. If the value is less than one, then block 528 executes where LAT is set to be the time of Max dV/dt. Block 530 then executes where $DV/DT_{MIN}$ is set to equal minus Max dV/dt. The negative sign is to ensure the same sign regardless of +/−EGM maximum slope. If the ratio is determined to be greater than or equal to one, then at block 532, LAT is set to be the time of Min dV/dt. Then at block 534 DV/DT$_{MIN}$ is set to equal Min dV/dt.

Advantageously, cardiac mapping techniques may be used to map the Local Activation Times and the values for Min dV/dt to particular points of the heart so that Min dV/dt may be utilized as a separate metric indicative of a health of the underlying cardiac tissue at said points. For example, values for Min dV/dt above a threshold may be indicative of abnormal or diseased tissue, whereas below said threshold may be indicative of normal or healthy tissue. In one embodiment, the threshold may be said to be 1 mv/ms. As will be understood by one of ordinary skill in the art, the first derivative of the signals may be computed according to the following equation:

Equation for calculating the EGM derivative, dv/dt:

Least mean squared error (LSME) parabolic fit of data $$j\dot{E}GM_k = \sum_{i=1}^{n} i(jEGM_{k+i} - jEGM_{k-i})$$

where j EGM is the j$^{th}$ EGM, k is the sample time, and A is dependent on n.

The techniques disclosed herein may be used with systems that include graphical user interfaces for use by users to evaluate a patient's cardiac health and/or adjust cardiac therapy. As described herein with reference to FIG. 1, the exemplary systems and methods described herein may use display apparatus 122 including a graphical user interface. The graphical user interface may be configured to, among other things, present information for use in assisting a user in evaluating a cardiac a patient's cardiac health. For example, the graphical user interface may be configured to display Local Activation Times and values for Min dV/dt. Further, for example, the graphical user interface may be configured to display a spatial map of electrical activation times and values for Min dV/dt.

Figure 6:
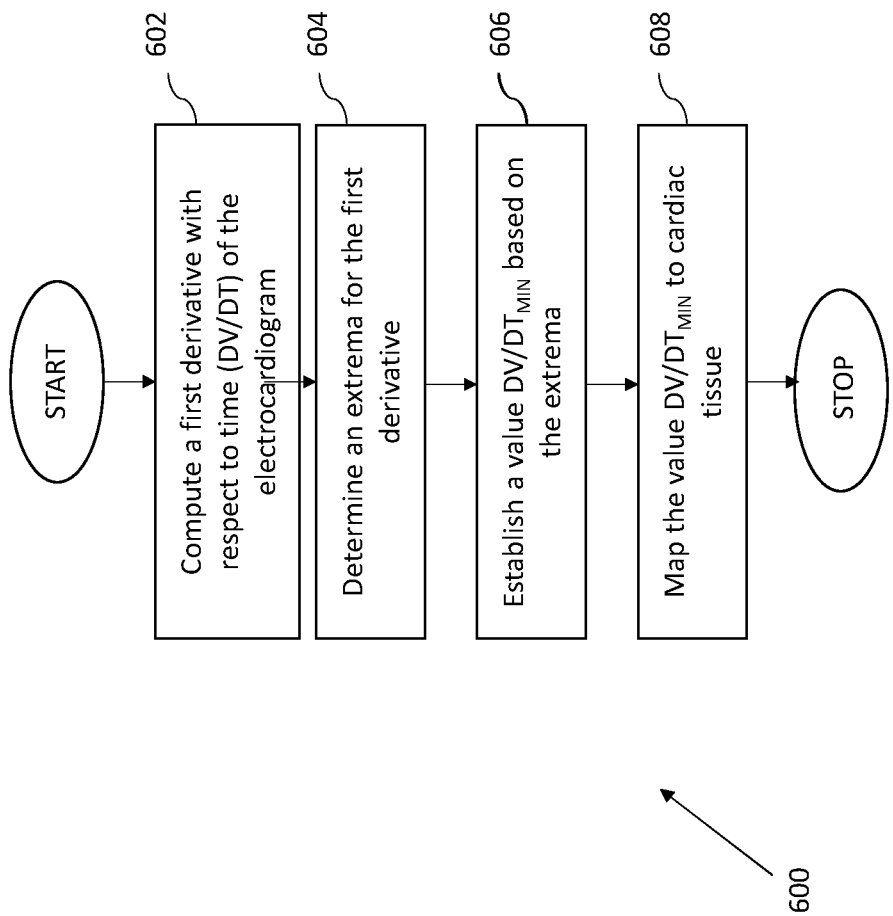
FIG. 6 shows a flowchart of key steps of the techniques illustrated and described with respect to FIGS. 5a-5c, in accordance with one embodiment of the invention.

FIG. 6 shows a flowchart of a method 700 for determining cardiac tissue health based on the depolarization wave within an EGM, in accordance with one embodiment. At block 602, a first derivative with respect to time (DV/DT) of the captured EGM is computed. At block 604, extrema are determined for the computed DV/DT of the EGM. At block 606 a minimum value of DV/DT (DV/DT$_{MIN}$) is established based on the determined extrema as described in detail in FIG. 4. At block 608, the value of DV/DT$_{MIN}$ is mapped to cardiac tissue.

Figure 7:
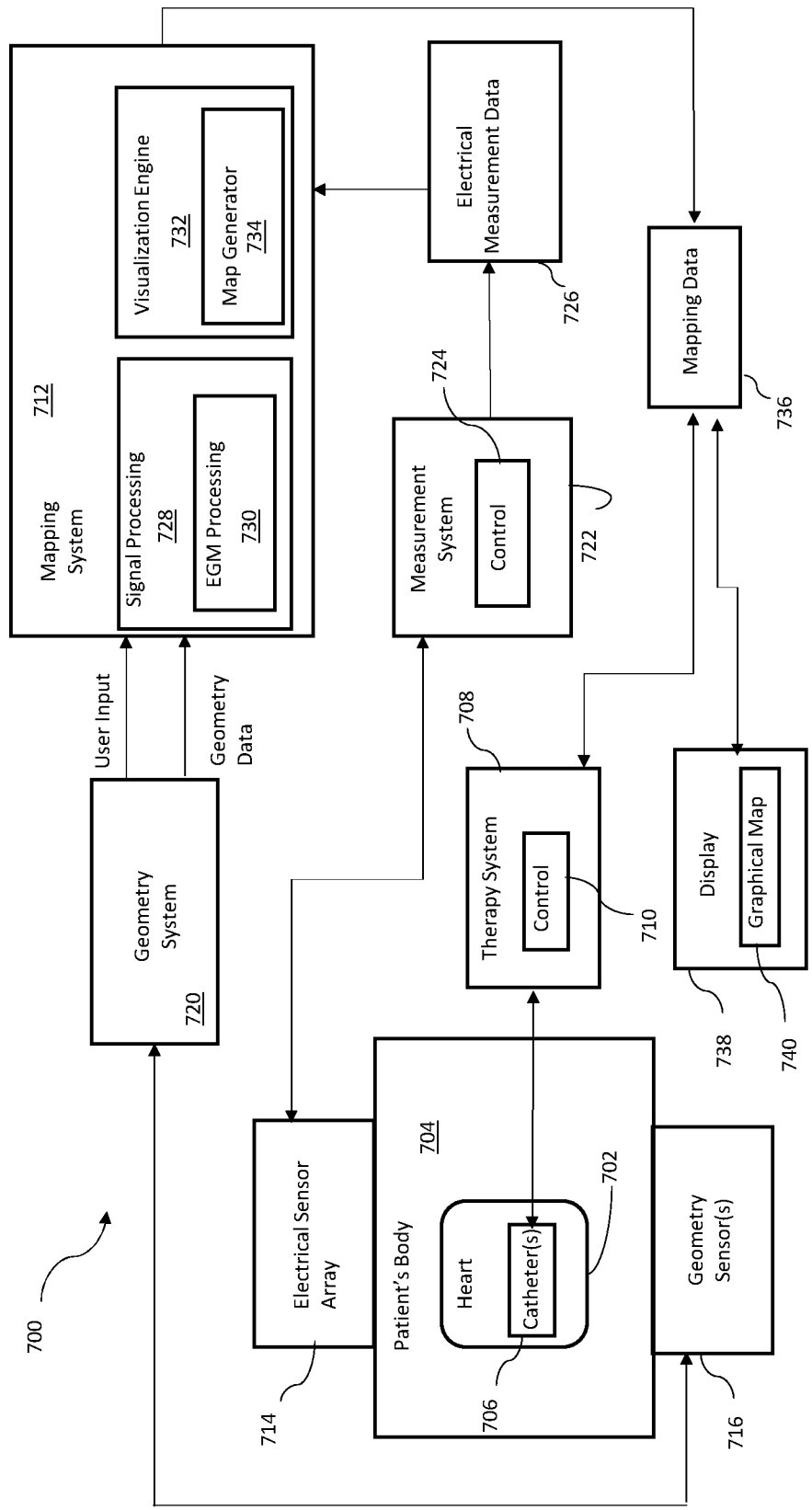
FIG. 7 of the drawings shows an exemplary diagnostic/treatment system, in accordance with one embodiment of the invention.

FIG. 7 of the drawings shows an exemplary diagnostic/treatment system 700, in accordance with one embodiment of the invention. The system 700 is capable of assessing the condition of the heart 702 in real-time as part of a treatment or diagnostic procedure. For this purpose, the system 700 includes one or more catheters that can be inserted into a patient's body 704 thereby to contact the patient's heart 702—more specifically the endocardium or the epicardium. One of ordinary skill in the art would understand and appreciate that various types and configurations of catheters 706 may be utilized, depending on the type of treatment and procedure.

In some cases, the therapy system 706 may include one or more electrodes located at the tip of an ablation catheter which in use is configured to ablate tissue in response to electrical signals (for example radiofrequency energy) supplied by a therapy system 708. In other cases, the therapy delivery device 706 may include one or more electrodes located at the tip of a pacing catheter to deliver electrical stimulation for pacing the heart in response The therapy system 708 may be located external to the patient's body 704 and may be configured to control the type of therapy that is delivered by the device 706. For example, the therapy system 708 may include control circuitry 710 configured to deliver electrical signals by a conductive link electrically connected between the device (electrodes) 706 and the therapy system 708. The control circuitry 710 may provide control parameters for the signals supplied to the device 706 (these may include current, voltage, etc.) For delivering therapy (example ablation) via the electrode (s) 704 to one or more sites within the heart 702, the control circuitry 710 may set therapy parameters and apply stimulation based on automatic, manual (user input) or a combination of automatic and manual mechanisms. In some embodiments, one or more sensors (not shown) may be configured to communicate since the information back to the therapy system 708. The position of the catheter 706 within the heart 702 may be determined and tracked by a mapping system 702. Location of the device 706 and in the therapy parameters may be combined to provide corresponding therapy parameters data.

In some embodiments, prior to providing therapy by the therapy system 708 and other system or subsystem may be utilized to acquire electrophysiological data for the patient. For this purpose, a sensor array 714 including one or more electrodes may be utilized for recording patient activity. In some cases, the sensor array 714 may include an arrangement of body surface sensors distributed over a portion of the patient's torso for measuring electrical activity associated with the patient's heart. The catheter 706 may include one or more electrodes that can be utilized in conjunction with the sensor array 714 for mapping electrical activity of the endocardial surface such as the wall of the heart chamber. Additionally, such electrodes may be used to obtain location or positional information of the catheter 706 within the heart which can advantageously be used to register electrical information of the heart in an image or map is generated by the system 700. In some embodiments, to facilitate the tracking of the catheter 706 positional within the heart, geometry sensors 716 may be positioned around the patient's body and configured to sense the position of the catheter 706 within the heart. For example, in some embodiments, the catheter 706 may be comprise with a magnetic element that can be sensed by the geometry sensors 716 to the to derive catheter positional data that is transmitted to a geometry system 720. The geometry system 720 may be configured to generate geometry data which is then input into the mapping systems 712.

In one embodiment, the sensor array 714 may be configured to provide the sensed electrical information to a corresponding measurement system 722. The measurement system 722 may include control circuitry 724 and signal processing circuitry (not shown) for generating electrical measurement data 726 that describes electrical activity detected by sensors in the sensor array 714. The electrical measurement data 726 may comprise analog and/or digital information. In some embodiments, the control circuitry 724 may be configured to control a data acquisition process for measuring electrical activity of the heart and generating the electrical measurement data 726. The electrical measurement data 726 may be acquired concurrently with the therapy delivered by the therapy system 708.

The mapping system 712 may be configured to combine the electrical measurement data 726 with geometry data generated by the geometry system 720 by applying appropriate processing computations. For example, the mapping system 712 may include a single processing module 728 configured to process the signals generated by the geometry system 720 and measurements system 722. For example, the signal processing module 728 may include an EGM processing module 730 configured to process EGM signals associated with the heart in accordance with the techniques described above including calculating DV/DT. A visualize relation engine 732 of the mapping systems and 712 may be provisioned with a mapped generator function 734 configured to render various metrics associated with the heart in visual form. For this purpose, the visualization engine 732 outputs mapping data 736 that can be rendered on a display 738 as a graphical map 740 showing various metrics associated with the heart.

By way of example, the geometry data output but the geometry system 720 may comprise a graphical representation of the patient's torso in the form of image data acquired for the patient. In one embodiment, the geometry system 720 may process the image data to extract and segment anatomical features of the heart. Additionally, positional information for the sensors within the electrical sensor array 714 may be included in the geometry data. The geometry data may be converted into a two-dimensional or three-dimensional graphical representation that includes regions of interest within the patient's heart by the mapping systems 712.

In other embodiments, the geometry data may include a mathematical model of the patient's heart instructed based on image data for the patient. Anatomical or other landmarks, including locations for the electrodes within the sensor array 714 may be identified in the geometry data to facilitate registration of the electrical measurement data 726. Identification of said landmarks may be performed manually based on the user input, or automatically by means of image processing techniques.

The mapped generator 734 may be configured to generate activation maps for the patient's heart, showing various metrics such as electrical activation times, and indications for QRS onset, the DV/DT, fractionation, etc.

In some embodiments, the system 100 acquiring cardiac signals described above may be embedded within the system 700.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware, such as shown and described with respect to the computer system of FIG. 8.

Figure 8:
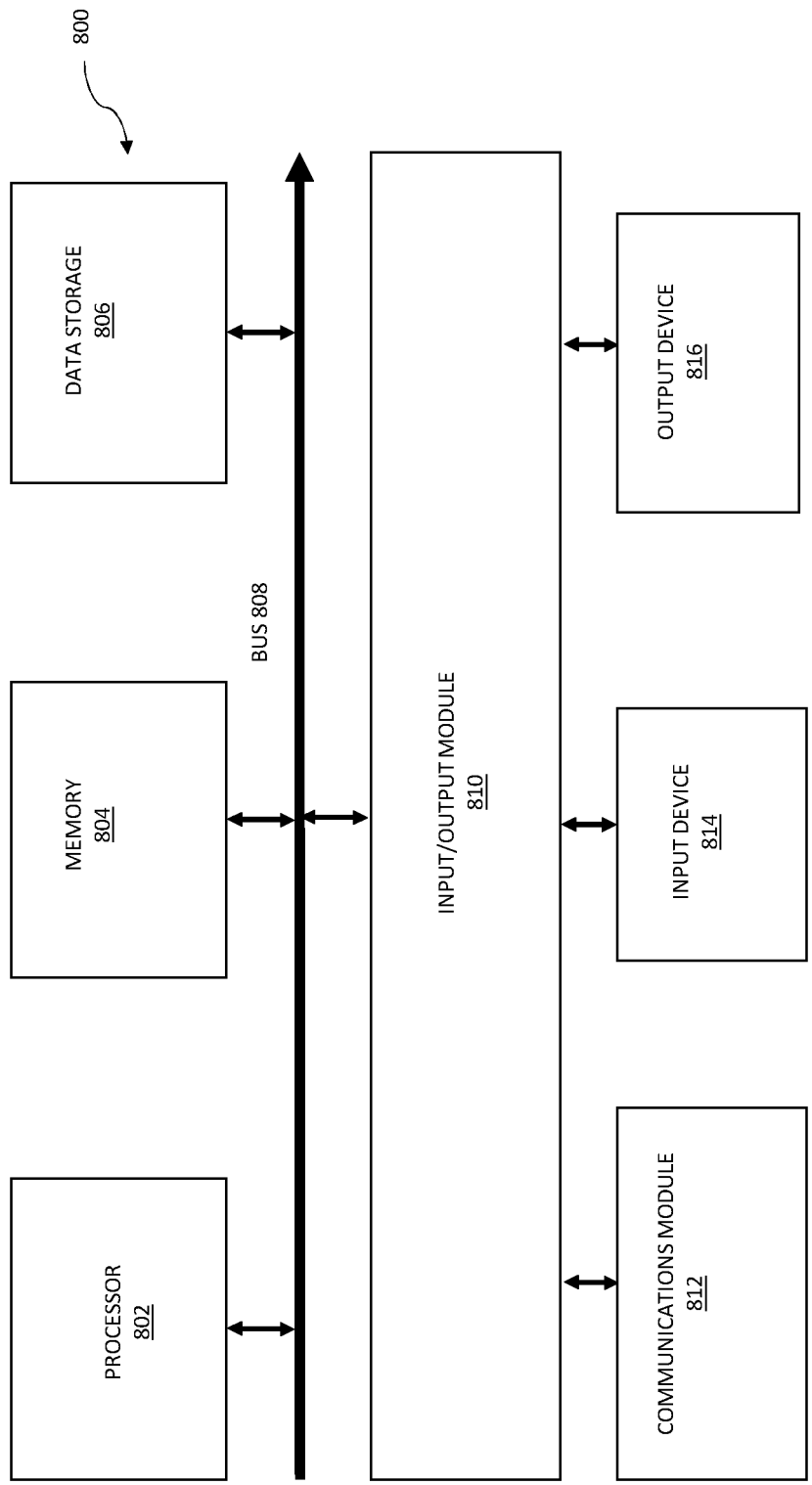
FIG. 8 shows a high-level block diagram of hardware that may be used to practice aspects of the present invention.

FIG. 8 is a block diagram illustrating, exemplary hardware for executing some of the techniques disclosed herein, in accordance with one embodiment of the invention. In certain aspects, the computer system 800 may be implemented using hardware or a combination of software and hardware, either in a dedicated server or integrated into another entity or distributed across multiple entities.

Computer system 800 (e.g., client or server) includes a bus 808 or other communication mechanism for communicating information, and a processor 802 coupled with bus 808 for processing information. According to one aspect, the computer system 800 may be implemented as one or more special-purpose computing devices. The special-purpose computing device may be hard-wired to perform the disclosed techniques, or may include digital electronic devices such as one or more application-specific integrated circuits (ASICs) or field programmable gate arrays (FPGAs) that are persistently, programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques. By way of example, the computer system 800 may be implemented with one or more processors 802. Processor 802 may be a general-purpose microprocessor, a microcontroller, a Digital Signal Processor (DSP), an ASIC, a FPGA, a Programmable Logic Device (PLD), a controller, a state machine, gated logic, discrete hardware components, or any other suitable entity that can perform calculations or other manipulations of information.

Computer system 800 can include, in addition to hardware, code that creates an execution environment for the computer program in question, e.g., code that constitutes processor firmware, a protocol stack, a database management system, an operating system, or a combination of one or more of them stored in an included memory 804 such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 808 for storing information and instructions to be executed by processor 802. The processor 802 and the memory 804 can be supplemented by, or incorporated in, special purpose logic circuitry. Expansion memory may also be provided and connected to computer system 800 through input/output module 810, which may include, for example, a SIMM (Single in Line Memory Module) card interface. Such expansion memory may provide extra storage space for computer system 800 or may also store applications or other information for computer system 800. Specifically, expansion memory may include instructions to carry out or supplement the processes described above and may include secure information also. Thus, for example, expansion memory may be provided as a security module for computer system 800 and may be programmed with instructions that permit secure use of computer system 800. In addition, secure applications may be provided via the SIMM cards, along with additional information, such as placing identifying information on the SIMM card in a non-hackable manner.

The instructions may be stored in the memory 804 and implemented in one or more computer program products, i.e., one or more modules of computer program instructions encoded on a computer readable medium for execution by, or to control the operation of, the computer system 800, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, metaparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, embeddable languages, and xml-based languages. Memory 804 may also be used for storing temporary variable or other intermediate information during execution of instructions to be executed by processor 802.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 870 further includes a data storage device 806 such as a magnetic disk or optical disk, coupled to bus 808 for storing information and instructions. Computer system 800 may be coupled via input/output module 810 to various devices. The input/output nodule 810 can be any input/output module. Example input/output modules 810 include data ports such as USB ports. In addition, input/output module 810 may be provided in communication with processor 802, so as to enable near area communication of computer system 800 with other devices. The input/output module 810 may provide, for example, for wired communication in some implementations, or for wireless communication in other implementations, and multiple interfaces may also be used. The input/output module 810 is configured to connect to a communications module 812. Example communications modules 812 include networking interface cards, such as Ethernet cards and modems.

The components of the system can be interconnected by any form or medium of digital data communication, e.g., a communication network. The communication network can include, for example, any one or more of a PAN, a LAN, a CAN, a MAN, a WAN, a BBN, the Internet, and the like. Further, the communication network can include, but is not limited to, for example, any one or more of the following network topologies, including a bus network, a star network, a ring network, a mesh network, a star-bus network, tree or hierarchical network, or the like.

For example, in, certain aspects, communications module 812 can provide a two-way data communication coupling to a network link that is connected to a local network. Wireless links and wireless communication may also be implemented. Wireless communication may be provided under various modes or protocols, such as GSM (Global System for Mobile Communications), Short Message Service (SMS), Enhanced Messaging Service (EMS), or Multimedia Messaging Service (MMS) messaging, CDMA (Code Division Multiple Access), Time division multiple access (TDMA), Personal Digital Cellular (PDC), Wideband CDMA, General Packet Radio Service (GPM), or LIE (Long-Term Evolution), among others. Such communication may occur, for example, through a radio-frequency transceiver. In addition, short-range communication may occur, such as using a BLUETOOTH, WI-FI, or other such transceiver.

In any such implementation, communications module 812 sends and receives electrical, electromagnetic or optical signals that carry digital data streams representing various types of information. The network link typically provides data communication through one or more networks to other data devices. For example, the network link of the communications module 812 may provide a connection through local network to a host computer or to data equipment operated by an Internet Service Provider (ISP). The ISP in turn provides data communication services through the world-wide packet data communication network now commonly referred to as the Internet. The local network and Internet both use electrical, electromagnetic or optical signals that carry digital data streams. The signals through the various networks and the signals on the network link and through communications module 812, which carry the digital data to and from computer system 800, are example forms of transmission media.

Computer system 800 can send messages and receive data, including program code, through the network(s), the network link and communications module 812. In the Internet example, a server might transmit a requested code for an application program through Internet, the ISP, the local network and communications module 810. The received code may be executed by processor 802 as it is received, and/or stored in data storage 806 for later execution.

In certain aspects, the input/output module 810 is configured to connect to a plurality of devices, such as an input device 812 (e.g., input device 814) and/or an output device 814 (e.g., output device 814). Example input devices 812 include a stylus, a finger, a keyboard and a pointing device, e.g., a mouse or a trackball, by which a user can provide input to the computer system 800. Other kinds of input devices 812 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 814 include display devices, such as a LED (light emitting diode), CRT (cathode ray tube), LCD (liquid crystal display) screen, a TFT LCD (Thin-Film-Transistor Liquid Crystal Display) or an OLED (Organic Light Emitting Diode) display, for displaying information to the user. The output device 814 may comprise appropriate circuitry for driving the output device 814 to present graphical and other information to a user.

According to one aspect of the present disclosure, the techniques disclosed here in may be implemented on the computer system 800 in response to processor 802 executing one or more sequences of one or more instructions contained in memory 804. Such instructions may be read into memory 804 from another machine-readable medium, such as data storage device 806. Execution of the sequences of instructions contained in main memory 804 causes processor 802 to perform the process steps described herein. One or more processors in a multi-processing arrangement ma also be employed to execute the sequences of instructions contained in memory 804. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components.

Computing system 800 can include clients and servers. A client and server are generally remote from each other and typically interact through a communication network. The relationship of client and server arises by virtue of computer programs running on the respective computers and having a client-server relationship to each other. Computer system 800 can be, for example, and without limitation, a desktop computer, laptop computer, or tablet computer. Computer system 800 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer-readable medium" as used herein refers to any medium or media that participates in providing instructions or data to processor 802 for execution. The term. "storage medium" as used herein refers to any non-transitory media that store data and/or instructions that cause a machine to operate in a specific fashion. Such a medium may take many forms, including, but not limited to, non-volatile media, volatile media, and transmission media. Non-volatile media include, for example, optical disks, magnetic disks, or flash memory, such as data storage device 806. Volatile media include dynamic memory, such as memory 804. Transmission media include coaxial cables, copper wire, and fiber optics, including the wires that comprise bus 808. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter affecting a machine-readable propagated signal, or a combination of one or more of them.

As used in this specification of this application, the terms "computer-readable storage medium" and "computer-readable media" are entirely restricted to tangible, physical objects that store information in a form that is readable by a computer. These terms exclude any wireless signals, wired download signals, and any other ephemeral signals. Storage media is distinct from but may be used in conjunction with transmission media. Transmission media participates in transferring information between storage media. For example, transmission media includes coaxial cables, copper wire and fiber optics, including the wires that comprise bus 808. Transmission media can also take the form of acoustic or light waves, such as those generated during radio-wave and infra-red data communications. Furthermore, as used in this specification of this application, the terms "computer", "server", "processor", and "memory" all refer to electronic or other technological devices. These terms exclude people or groups of people. For the purposes of the specification, the terms display or displaying means displaying on an electronic device.

To illustrate the interchangeability of hardware and software, items such as the various illustrative blocks, modules, components, methods, operations, instructions, and algorithms have been described generally in terms of their functionality. Whether such functionality is implemented as hardware, software or a combination of hardware and software depends upon the particular application and design constraints imposed on the overall system. Skilled artisans may implement the described functionality in varying ways for each particular application.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C, any combination of A, B, and C; and/or at least one of each of A, B, and C.

To the extent that the term "include," "have," or the like is used in the description or the claims, such term is intended to be inclusive in a manner similar to the term "comprise" as "comprise" is interpreted when employed as a transitional word in a claim. Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A reference to an element in the singular is not intended to mean "one and only, one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. Relational terms such as first and second and the like may be used to distinguish one entity or action from another without necessarily requiring or implying any actual such relationship or order between such entities or actions. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description. No claim element is to be construed under the provisions of 35 U.S.C. § 112, sixth paragraph, unless the element is expressly recited using the phrase "means for" or, in the case of a method claim, the element is recited using the phrase "step for."

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub combination or variation of a sub-combination.

The subject matter of this specification has been described in terms of particular aspects, but other aspects can be implemented and are within the scope of the following claims. For example, while operations are depicted in the drawings in a particular order, this should not be understood as requiring that such operations be performed in the particular order shown or in sequential order, or that all illustrated operations be performed, to achieve desirable results. The actions recited in the claims can be performed in a different order and still achieve desirable results. As one example, the processes depicted in the accompanying figures do not necessarily require the particular order shown, or sequential order, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

The invention claimed is:

1. A method for determining cardiac tissue health based on a depolarization wave within an electrogram (EGM), comprising:
   receiving, by a processor, an electrogram (EGM), wherein the EGM comprises at least one of a unipolar EGM and a bipolar EGM;
   removing, by the processor, noise from the EGM when the noise is above a predefined threshold;
   computing, by the processor, a first derivative with respect to time (DV/DT) of the EGM;
   determining, by the processor, extrema for the first derivative, wherein the extrema comprises at least a maxima and a minima;
   based on the extrema, establishing, by the processor, a value $DV/DT_{MIN}$ by selecting at least one of
      the minima as the value for $DV/DT_{MIN}$ for the unipolar EGM;
      the maxima and the minima for the bipolar EGM as the value for $DV/DT_{MIN}$ based on a ratio; and
   mapping, by the processor, the value $DV/DT_{MIN}$ to cardiac tissue.

2. The method of claim 1, wherein the value for $DV/DT_{MIN}$ for the bipolar EGM is selected as Min dV/dt when the ratio |Min dV/dt|/|Max dV/dt| is greater than or equal to one.

3. The method of claim 1, wherein the value for $DV/DT_{MIN}$ for the bipolar EGM is selected as the −Max dV/dt when the ratio |Min dV/dt|/|Max dV/dt| is less than one.

4. The method of claim 1, wherein the noise is removed by applying a power line filter or a random noise filter to the EGM.

5. A system for determining cardiac tissue health based on a depolarization wave within an electrogram (EGM), comprising:
   a memory; and
   one or more processors coupled to the memory programmed with executable instructions to:
   receive an electrogram (EGM), wherein the EGM comprises at least one of a unipolar EGM and a bipolar EGM;
   remove noise from the EGM when the noise is above a predefined threshold;
   compute a first derivative with respect to time (DV/DT) of the EGM;
   determine extrema for the first derivative, wherein the extrema comprise at least a maxima and a minima;
   based on the extrema, establish a value $DV/DT_{MIN}$ by selecting at least one of
      the minima as the value for $DV/DT_{MIN}$ for the unipolar EGM;
      the maxima and the minima for the bipolar EGM as the value for $DV/DT_{MIN}$ based on a ratio; and
      map the value $DV/DT_{MIN}$ to cardiac tissue.

6. The system of claim 5, wherein the value for $DV/DT_{MIN}$ for the bipolar EGM is selected as Min dV/dt when the ratio |Min dV/dt|/|Max dV/dt| is greater than or equal to one.

7. The system of claim 5, wherein the value for $DV/DT_{MIN}$ for the bipolar EGM is selected as the $-Max\ dV/dt$ when the ratio $|Min\ dV/dt|/|Max\ dV/dt|$ is less than one.

8. The system of claim 5, wherein the noise is removed by applying a power line filter or a random noise filter to the EGM.

9. A non-transitory computer readable storage medium, having stored thereon, a set of computer-executable instructions that causes a computer to perform the method comprising:
 receiving an electrogram (EGM), wherein the EGM comprises at least one of a unipolar EGM and a bipolar EGM;
 removing noise from the EGM when the noise is above a predefined threshold;
 computing a first derivative with respect to time (DV/DT) of the EGM;
 determining extrema for the first derivative, wherein the extrema comprise at least a maxima and a minima;
 based on the extrema, establishing a value $DV/DT_{MIN}$ by selecting at least one of
 the minima as the value for $DV/DT_{MIN}$ for the unipolar EGM;
 the maxima and the minima for the bipolar EGM as the value for $DV/DT_{MIN}$ based on a ratio; and
 mapping the value $DV/DT_{MIN}$ to cardiac tissue.

10. The non-transitory computer readable storage medium of claim 9, wherein the value for $DV/DT_{MIN}$ for the bipolar EGM is selected as $Min\ dV/dt$ when the ratio $|Min\ dV/dt|/|Max\ dV/dt|$ is greater than or equal to one.

11. The non-transitory computer readable storage medium of claim 9, wherein the value for $DV/DT_{MIN}$ for the bipolar EGM is selected as the $-Max\ dV/dt$ when the ratio $|Min\ dV/dt|/|Max\ dV/dt|$ is less than one.

12. The non-transitory computer readable storage medium of claim 9, wherein the noise is removed by applying a power line filter or a random noise filter to the EGM.

* * * * *